(12) United States Patent
Gochberg

(10) Patent No.: US 11,585,881 B2
(45) Date of Patent: Feb. 21, 2023

(54) MAGNETIC RESONANCE IMAGING OF NEURO-ELECTRO-MAGNETIC OSCILLATIONS

(71) Applicant: Vanderbilt University, Nashville, TN (US)

(72) Inventor: Daniel Gochberg, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 259 days.

(21) Appl. No.: 17/073,164

(22) Filed: Oct. 16, 2020

(65) Prior Publication Data
US 2021/0116526 A1    Apr. 22, 2021

Related U.S. Application Data

(60) Provisional application No. 62/916,496, filed on Oct. 17, 2019.

(51) Int. Cl.
| | |
|---|---|
| *G01R 33/483* | (2006.01) |
| *G01R 33/48* | (2006.01) |
| *G01R 33/54* | (2006.01) |
| *A61B 5/055* | (2006.01) |
| *A61B 5/00* | (2006.01) |

(52) U.S. Cl.
CPC .......... *G01R 33/4833* (2013.01); *A61B 5/055* (2013.01); *A61B 5/4064* (2013.01); *G01R 33/4806* (2013.01); *G01R 33/543* (2013.01)

(58) Field of Classification Search
CPC ............ G01R 33/4833; G01R 33/4806; G01R 33/543; G01R 33/4608; A61B 5/055; A61B 5/4064
See application file for complete search history.

(56) References Cited

U.S. PATENT DOCUMENTS

| | | | |
|---|---|---|---|
| 6,528,997 B2 | 3/2003 | Zhong et al. | |
| 6,605,942 B1* | 8/2003 | Warren | G01R 33/4833 |
| | | | 324/307 |
| 10,175,319 B2 | 1/2019 | Truong et al. | |
| 2014/0296695 A1* | 10/2014 | He | A61B 5/4312 |
| | | | 324/318 |

FOREIGN PATENT DOCUMENTS

WO    WO-2011130633 A2 *  10/2011  ......... G01R 33/1284

OTHER PUBLICATIONS

Richter, Wolfgang, et al. "Functional magnetic resonance imaging with intermolecular multiple-quantum coherences." Magnetic resonance imaging 18.5 (2000): 489-494. (Year: 2000).*
Branca, Rosa T., et al. "In vivo noninvasive detection of brown adipose tissue through intermolecular zero-quantum MRI." PloS one 8.9 (2013): e74206. (Year: 2013).*

* cited by examiner

*Primary Examiner* — Rishi R Patel
(74) *Attorney, Agent, or Firm* — Blank Rome LLP

(57) ABSTRACT

In vivo methods for non-invasively imaging (or measuring without spatial localization) of neuro-electro-magnetic oscillations are achieved by a pulse sequence of radio frequency (RF) irradiation and magnetic field gradients. These RF and gradient pulses create an intermolecular zero-quantum coherence (iZQC), the frequency of which is: 1) controlled by one or more magnetic field gradients; and 2) made to match the frequency of the targeted neuro-electro-magnetic oscillation.

18 Claims, 1 Drawing Sheet

MAGNETIC RESONANCE IMAGING OF NEURO-ELECTRO-MAGNETIC OSCILLATIONS

CROSS REFERENCE TO RELATED APPLICATION(S)

This application claims priority to U.S. provisional patent application No. 62/916,496, filed on Oct. 17, 2019, which is hereby incorporated herein by reference in its entirety.

FIELD OF THE INVENTION

Embodiments are in the field of systems and methods for imaging. More particularly, embodiments disclosed herein relate to systems and methods for non-invasively imaging (or measuring without spatial localization) of neuro-electro-magnetic oscillations.

BACKGROUND OF THE INVENTION

Embodiments of the present disclosure employ an magnetic resonance imaging (MRI) pulse sequence that allows direct imaging of neuronal currents, i.e., neuro-electro-magnetic oscillations (NEMOs). The conventional MRI method for imaging neuronal activity is called "functional imaging" which is based on imaging increased blood flows to areas of the brain responsible for a particular neurological task. This hemodynamic response is indirect and coarse, both spatially and temporally. Functional imaging gives a general idea, but direct measurement would be much better. U.S. Pat. No. 10,175,319 issued to Truong et al. employs a pulse sequence aiming to achieve a similar goal of imaging neuronal currents. However, there are key differences between the present disclosure and the system/method described in the '319 patent.

The disclosure of the '319 patent describes a small variation/improvement in pulse sequences published previously by other entities developing neuronal current imaging techniques based on a spin-lock approach. The present disclosure employs a different implementation with a different physical basis, having nothing to do with the spin-lock phenomenon. Instead, it includes a distinct implementation (i.e., with different/additional acquisition parameter choices) of a pulse sequence to generate multiquantum coherences, which is also the goal of a different pulse sequence described in U.S. Pat. No. 6,528,997 issued to Zhong. However, it is noted that the pulse sequence in the '997 patent is not used for neuronal current imaging. The inventor recognizes that, when using the particular different/additional acquisition parameters, the pulse sequence described hereinbelow will be sensitive to the small NEMOs produced by neuronal currents. The system/method of the present disclosure creates intermolecular multiple quantum coherences (iMQC) that are specifically sensitive to neuronal currents. Specifically, the zero quantum coherence (iZQC) creates the neuronal current sensitivity. This approach to neuronal current imaging is completely novel as compared to the techniques described in the above-mentioned patents.

Thus, it is desirable to provide a system and method for non-invasively imaging (or measuring without spatial localization) of neuro-electro-magnetic oscillations that is able to overcome the above disadvantages.

Advantages of the present invention will become more fully apparent from the detailed description of the invention hereinbelow.

SUMMARY OF THE INVENTION

Embodiments are directed to a method for magnetic resonance imaging. The method includes applying a pulse sequence in vivo for exciting intermolecular zero-quantum coherence that are sensitive to neuro-electro-magnetic oscillations (NEMOs). The pulse sequence includes a plurality of radiofrequency (RF) pulses and a plurality of magnetic field gradients. The method also includes receiving signals that are sensitive to NEMOs, in response to the applying step. The method further includes forming a magnetic resonance image of the NEMOs using the received signals.

Embodiments are also directed to a system for magnetic resonance imaging. The system includes at least one coil configured to apply a pulse sequence in vivo for exciting intermolecular zero-quantum coherence that are sensitive to neuro-electro-magnetic oscillations (NEMOs). The pulse sequence includes a plurality of radiofrequency (RF) pulses and a plurality of magnetic field gradients. The system also includes a receiver configured to receive signals that are sensitive to NEMOs, in response to the pulse sequence application. The system further includes a magnetic resonance imaging device configured to form a magnetic resonance image of the NEMOs using the received signals.

Additional embodiments and additional features of embodiments for the method for magnetic resonance imaging and system for magnetic resonance imaging are described below and are hereby incorporated into this section.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It is understood, however, that the inventive concepts disclosed herein are not limited to the precise arrangements and instrumentalities shown in the figures. The detailed description will refer to the following drawings in which like numerals, where present, refer to like items.

DETAILED DESCRIPTION OF THE INVENTION

Figure 1:
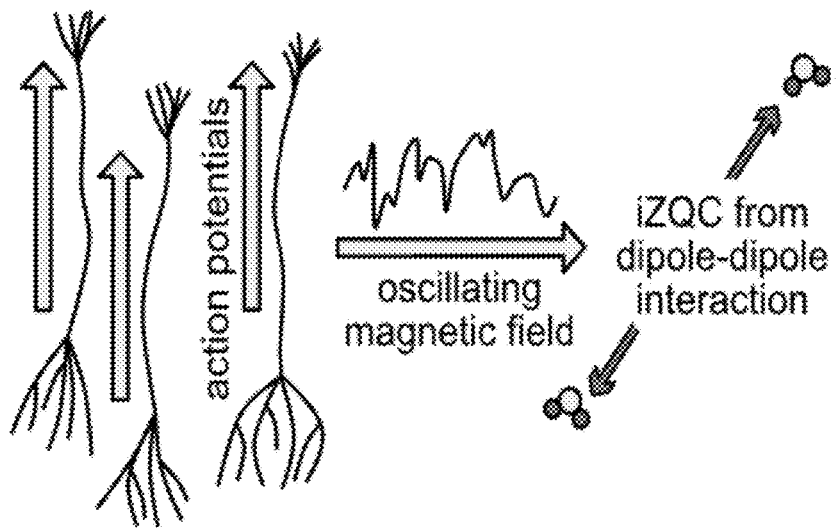
FIG. 1 is a drawing illustrating action potential currents which generate oscillating magnetic fields that have a resonant effect on tuned iZQCs.

It is to be understood that the figures and descriptions of the present invention may have been simplified to illustrate elements that are relevant for a clear understanding of the present invention, while eliminating, for purposes of clarity, other elements found in a typical system for MRI or typical method of using or operating a system for MRI. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented devices, systems, methods, features, and advantages will be or become apparent to one with skill in the art upon examining the drawings and the detailed description herein. It is intended that all such additional devices, systems, methods, features, and advantages be protected by the accompanying claims.

Embodiments of the invention are directed to MRI neuroimaging systems, circuits and protocols that can noninvasively image neuroelectric activity (such as NEMOs) with a high spatial and temporal resolution, which may be particularly suitable for evaluating and/or studying the human brain.

Embodiments of the invention are directed to in vivo MRI protocols that can noninvasively image magnetic field oscillations resulting from neuroelectric activity (such as NEMOs), in one or more defined frequency bands.

Embodiments of the invention provide pulse sequences for MR Scanners for obtaining MRI image signals that can accurately localize neuronal activity (i.e., neuronal currents) with high spatial and temporal resolution in neuroactivation maps.

Embodiments of the invention may include MRI data acquisition and processing methods, circuits and systems that can directly image neuroelectric activity (such as NEMOs).

Embodiments may include an image processing circuit configured to electronically carry out any of the methods described herein.

Embodiments may include an MR image processing system that includes at least one processor configured to carry out any of the methods described herein.

The activation map can be a brain activation map having high temporal and spatial accuracy of the neuroelectric activity (such as NEMOs).

The subject can be human or animal.

An MR image of the NEMOs may be in the form of a 2D image or 3D image, and may use any of several possible imaging encoding methods, including gradient-echo, spin-echo, spiral, or echo-planar imaging. NEMOs may also be spatially localized using gradients but without full imaging.

Embodiments may include an MRI image processing system in communication with and/or at least partially on-board an MRI Scanner, including at least one processor configured to carry out any of the methods described herein.

Embodiments may include a data processing system that includes a non-transitory computer readable storage medium having computer readable program code embodied in the medium. The computer-readable program code may include computer readable program code configured to carry out any of the methods described herein.

The present disclosure describes a novel magnetic resonance imaging technique of direct imaging neuronal currents with the goal of increasing both sensitivity and specificity, such that the imaging technique is not sensitive, or has limited sensitivity, to confounding factors such as blood flow issues within a brain.

By employing a pulse sequence including a series of RF pulses and gradient pulses, the present disclosure creates a resonance condition to neuronal frequencies that hasn't been contemplated before. The process uses, inter alia, the intermolecular zero-quantum coherence phenomenon which has, to a limited degree, been used previously but only for other purposes not connected to imaging of neuronal currents.

The '997 patent uses gradients as an essential part of a sequence, but the patent does not use the gradients to set a resonant frequency for the interacting spins, which is an important aspect of the present approach. The present design allows for setting the target frequency under user control such that the technique is sensitive to oscillations only within a limited bandwidth around this target frequency and hence picks up only neuronal currents. The '997 patent describes the use of gradients in order to create and select for intermolecular multi-quantum coherences (which the present invention also contemplates) but the '997 patent doesn't use it to control the frequency of that interaction.

Figure 2A:
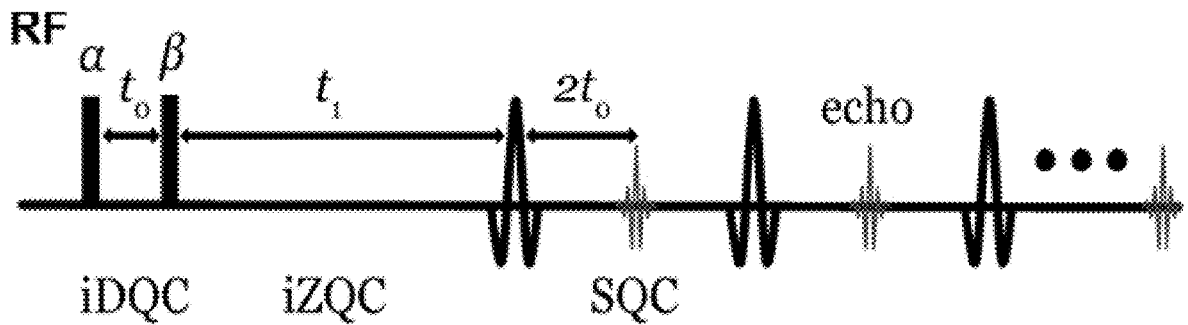
FIG. 2A is a plot illustrating the pulse sequence generating periods of zero, single, and double quantum coherence (indicated by iZQC, SQC, and iDQC, respectively). The duration $t_1$ and frequency of the ZQC evolution are independently controlled using the applied gradients in FIG. 2B.

The '997 patent images double-quantum coherences (iDQC), while the present invention uses zero-quantum coherences (iZQC) for the essential sensitivity to neuronal currents. It is noted, however, that the sequence in the present invention in FIG. 2A below also does use double quantum coherences as part of a filtering mechanism to avoid confounding signal contributions and to dictate the spin interaction distance of the iZQC's. This use of iZQC instead of iDQC for the essential sensitivity makes the present invention a significantly different pulse sequence for at least the following reasons: 1) it uses different RF pulse amplitudes, phases, and timings; and 2) the iZQC is a distinct phenomenon and is resonant at the difference of the Larmor frequencies of the interacting spins, while the iDQC is resonant at the sum.

An important goal of the present disclosure is to make the signal highly dependent on oscillations at neuronal frequencies and less dependent on everything else, so as not to interfere with the imaging of the NEMOs.

The frequency of the pulse sequence of the present invention is operable at 100 Hz and less, which is where one expects to see neuronal currents, although other frequency ranges such as 0.5 Hz-1000 Hz may also be contemplated. Embodiments of the present disclosure may benefit from increases in field strength. A large benefit of using a high field strength with the 2-spin phenomenon is that the iZQC signal scales quadratically rather than linearly with an increase in the static field strength. It should be understood that the targeted neuronal currents are very small and create small magnetic fields on a scale of 0.1-1 nT.

Figure 2B:
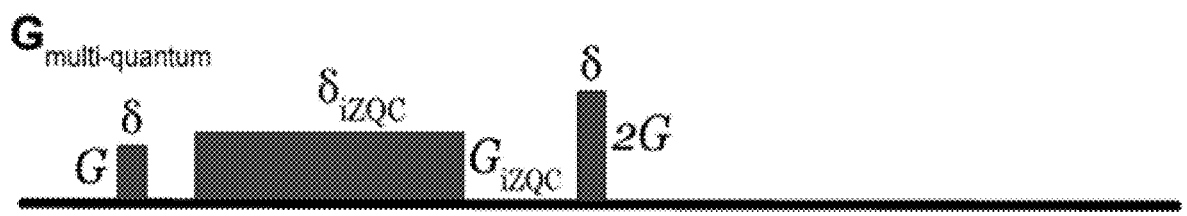

The pulse sequence may or may not include spatial localization as desired. This localization may include slice selection and/or imaging gradients. The pulse described in FIG. 2A below is a pre-pulse before any such spatial localization is performed. Anything performed without slice-selection or imaging gradients (such as any MR imaging), can also be done with such imaging gradients. If imaging or spatial localization is desired, corresponding slice-select, phase-encode, and readout gradients can be added (in addition to the multi-quantum gradients in FIG. 2B) following standard approaches.

Overview

This disclosure describes a novel method for mapping neuronal electrical activity at high spatial resolution using MRI, and achieves the direct detection of neuronal currents using a previously unexplored mechanism based on resonant two-spin interactions. While established functional MRI (fMRI) methods have greatly benefited neuroscience, they detect neuronal activity only indirectly based on hemodynamic responses. Consequently, fMRI has limited spatial and temporal resolutions, and is not a direct indication of the underlying electrical signals. The ability to directly image neuronal currents may profoundly advance the understanding of fundamental neural processes.

These potential benefits have motivated several previous magnetic resonance approaches, but to date no method has clearly demonstrated viable direct imaging of neuronal currents. Sensitivity and specificity issues have stymied these previous approaches. Neuronal currents cause magnetic fields on the scale of 0.1 to 1 nT, roughly 10 orders of magnitude smaller than typical static MRI fields, thereby creating a fundamental technical challenge. Physiologic noise and concurring processes, such as blood flow changes, generate further specificity challenges. Addressing the sensitivity issue by increasing the static field strength is limited by homogeneity requirements, and would not address the specificity issue, since confounding blood flow effects also scale with field strength. Instead, a new approach is necessary that is highly sensitive and specific to the characteristics of neural signals.

The disclosure describes a method based on two-spin intermolecular zero quantum coherences (iZQC), which is a physical phenomenon fundamentally different than any previous neuronal current imaging mechanism. This novel approach has four major benefits: 1) it can be designed to be resonant with neural frequency bands (e.g., alpha, beta, and so on, which are 10's of Hz), thereby filtering out the otherwise overwhelming background magnetic environment; 2) since iZQC is a multiple quantum coherence, conventional single quantum coherences (which are the basis for fMRI) can be filtered from the signal, reducing confounding hemodynamic effects; 3) being a two-spin effect, the magnitude of the iZQC signal scales like the square of the static magnetic field, greatly increasing the sensitivity and specificity at very high fields; and 4) since the iZQC evolves at the frequency difference of two nearby spins, it is remarkably robust to the field inhomogeneity issues that have typically limited very high field approaches.

Neuronal Current Imaging

As mentioned above, fMRI has revolutionized neuroscience by enabling non-invasive mapping of neuronal activity. However, this mapping is indirect, based on hemodynamic effects, and the resulting images are coarse. The spatial correspondence to the underlying neuronal activity is often unclear, making the images effectively low resolution (though the nominal resolution can be sub-millimeter in specialized situations). Additionally, fMRI has low temporal resolution, since it reflects changes in capillary blood flow (1-2 s) and typically uses acquisition times of tens of seconds. Transient fMRI methods can record changes of <100 ms, but are modulated by the hemodynamic response, which may, for example, flip the apparent timing of the visual and motor responses to stimuli. While electroencephalography (EEG) and magnetoencephalography (MEG) make direct measurements of electrical and magnetic effects, they do so on the outside surface, with limited ability to localize the neuronal source. A more informative method would directly map neuronal firing, a goal that has attracted interest for decades in the magnetic resonance (MR) community. However, using MR is inherently challenging due to the small magnetic fields generated by spontaneous neuronal oscillations (roughly 0.1 to 1 nT) and the difficulty in distinguishing neuronal current effects from other confounding signals.

How the iZQC Approach Relates to the Prior References and why it Works

Many groups have tried to image neuronal currents using magnetic resonance, but have had limited success due to their difficulties separating neuronal effects from confounding physiologic noise (including but not limited to blood oxygen level dependent (BOLD) effects), especially in light of signal-to-noise ratio (SNR) constraints. Increasing the SNR by moving to higher fields is limited by the coinciding increase in confounding effects and the need for high static field homogeneity. Not counting biomechanical/biochemical approaches that are arguably less direct (such as those based on the Lorentz force, diffusion, conductivity changes, and manganese influx or other agent effects), previous methods fall into two general categories: phase accumulation and resonant effects.

Phase Accumulation

Most MR approaches have been based on phase accumulation in the signal due to small changes in the field parallel to the static magnetic field $B_0$. Early work applied DC currents in phantoms and oscillating currents in tissue models. Moving this work in vivo proved difficult and with unclear results. A core issue is specificity, i.e. how to separate the effects of neuronal currents from other confounding factors. Time-based filtering was used to separate transient currents (~40 ms) from slower changing fields in order to minimize contributions from hemodynamic effects, along with respiration and subject motion. An fMRI type design had been used, but with a 2 s cycle in order to minimize contributions from slow hemodynamic responses. Further, such studies may also have subtle confounding contributions from fresh blood inflow, variations in water bound to macromolecules, and cell swelling. Finally, a complex modeling of phase accumulation from neuron generated magnetic fields concluded that different approaches should be explored for successful and clear neuronal current imaging. In sum, phase accumulation approaches have not clearly separated neuronal current effects from confounding signal contributions.

Resonant Effects

While neuronal oscillations have a broad spectrum, the key to separating neuronal current effects from confounding signal contributions is to leverage the narrow spectral content of particular bands, most notably alpha (8-12 Hz), but also delta (1-4 Hz), theta (4-8 Hz), beta (13-30 Hz), and gamma (30-70 Hz). A previous technique used the frequency dependence of phase effects to try to isolate contributions from these bands. However, several groups have taken a different approach, using band-specific resonant excitation and relaxation.

A resonant approach that is conceptually simple but experimentally complex is ultra-low field (ULF) magnetic resonance. One previous approach simply lowered the static magnetic field until the Larmor precession frequency matched the neuronal oscillations, thus allowing the neuronal currents to resonantly excite the spins. Experimentally, this is very tricky, since such low static fields produce very little spin polarization and thus low signal. Hence, a large prepolarizing field was used, along with superconducting quantum interference devices (SQUIDs) to maximize sensitivity. Even then, a static field of 100 µT was required (which produces a precession frequency roughly 100 times larger than typical neuronal oscillating bands). While this line of research continues, ULF based neuronal current imaging is experimentally exotic and unlikely to yield application soon.

Another approach (and one that uses typical MRI fields) creates magnetic resonance in the doubly-rotating frame. (This approach is also referred to as "spin-locking", "rotary saturation", or "$T_{1\rho}$ saturation".) These methods have a tunable resonance in the 10s of Hz range to try to isolate the effects of alpha band currents. This specific frequency sensitivity is controlled by the magnitude of the applied RF field, which creates a magnetic resonance condition in the doubly-rotating frame (i.e. after rotations about the lab z-axis and the RF field effective field direction). This controllable resonance is a huge advantage over the phase accumulation methods, since it filters out much of the background physiologic noise. However, recent attempts to validate the approach in vivo have had mixed results, with physiologic specificity a key issue.

The Proposed iZQC Resonant Approach

Like the ULF and doubly-rotating frame methods, the proposed approach has a tunable resonance that potentially can be used to separate the effects of neuronal firing from that of background physiologic phenomenon. However, the iZQC resonance at neuronal frequencies has a fundamentally different physical basis than previous work, and the inventor hypothesizes that it can address the core issues that have stymied previous methods. Specifically, iZQC's have the benefit of being resonant with the frequency of the neuronal oscillations without requiring the static field homogeneity, and hence relatively low static field strengths, needed by previous resonant methods. By being a two-spin phenomenon, the iZQC approach is viable in extremely inhomogeneous fields and hence allows for greatly increasing the static field strength and/or acquiring data over very large regions of interest. The ability to acquire iZQC over large regions and at ultra-high and unstable field strengths has been leveraged in previous works for spectroscopic measurements. In the current context, the present disclosure leverages these same effects for detecting neuronal currents.

A core of this disclosure is that neuronal currents have a resonant interaction with iZQC's and that this mechanism has an effectiveness that is frequency dependent and hence tunable via the applied gradient strength. The pulse sequence and mechanism underlying this resonant interaction are outlined in the APPROACH section below.

Innovation

Novel Methodology Based on Two-Spin Phenomenon Resonant to Neuronal Frequencies iZQC's have had applications largely limited to generating structural-anatomical image contrast and metabolic spectroscopy signals over large regions with inhomogeneous static magnetic fields. A key to this disclosure is the recognition that two-spin iZQC's: 1) can have a resonant interaction with the magnetic fields generated by low-frequency neural bands; 2) are likely to avoid some of the limitations of single-quantum doubly-rotating approaches described above; and 3) will have a quadratically increased signal at ultra-high fields, leveraging recent hardware advances. iZQC's are a new mechanism for neuronal current imaging, and neuronal current imaging is a new use for iZQCs.

Approach

General Idea

This disclosure describes a novel approach to direct detection of oscillating neuronal currents based on iZQCs that have a resonance tuned to match low-frequency bands, e.g. the alpha band at 8 to 12 Hz. FIG. 1 diagrams the general idea.

iZQC iZQC is a particular type of intermolecular multi-quantum coherence (iMQC), a phenomenon that was discovered in the 1990s and is based on long range dipolar couplings in unrestricted liquid samples. Previously, it was commonly believed that dipolar couplings in liquids rapidly averaged to zero, and hence could not generate coherent evolutions as is necessary to generate multi-quantum coherences. Instead, it was believed that multi-quantum dipole-dipole phenomenon were limited to restricted spin systems, such as in macromolecules. The key insights overturning these ideas were: 1) avoiding the high temperature approximation previously used to characterize the spin state; and 2) recognizing that applied gradients destroy the spatial symmetry that would otherwise cancel long range dipolar field effects. These insights were fully developed over the next couple decades. The key result from these developments is that the inventor can now use well-established pulse sequences to create iZQCs, and the disclosure describes the details of the planned implementation and modification of such a sequence below.

Physics of iZQC Sensitivity to Low Frequency Bands

The full physics underlying iZQC phenomenon is complex. The key characteristics of iZQCs for this disclosure's purposes are that: 1) they resonate at the difference in the Larmor frequencies of two interacting spins; 2) the spatial separation of these interacting spins is controlled by applied gradients; and 3) the difference in the Larmor frequencies (during the gradient application) is also controlled by the gradients, which has not been previously known. While these characteristics are true for all pulse sequences that generate iZQCs, and the inventor could use any such sequence for embodiments of this disclosure, this disclosure employs a particular sequence that uses two distinct gradients to separately control the interacting spins' spatial separation and frequency difference, allowing optimization of each acquisition parameter, including maximizing the duration of neuronal current sensitivity.

Pulse Sequence

This disclosure describes a method for detecting neuronal currents. One possible implementation of this method uses the pulse sequence diagrammed in FIG. 2A. To detect iZQC with this sequence, the inventor made two major changes in a previously developed pulse sequence. First, as can be confirmed using standard 2D spectroscopy techniques, the sequence has the ability to independently control the iZQC resonant frequency and duration. This independent control is novel and is based on using the intermolecular double quantum coherence (iDQC) to dictate the "correlation distance" $d_c = \pi/(\gamma G\delta)$, where G and $\delta$ (see, for example, FIG. 2B) are the first multi-quantum gradient amplitude and duration, respectively, $\gamma$ is the gyromagnetic ratio, and $d_c$ dictates the rough separation distance of the protons whose dipole-dipole interaction generates the quantum coherence. The frequency of the iZQC (and the resonance to neuronal currents) is then dictated by $d_c$ and the second gradient amplitude $G_{iZQC}$, independent of duration. Additionally, the train (echo) of refocusing pulses are added to extend the acquisition window and diminish the diffusion-based attenuation during the build-up of the multi-quantum signal while, more importantly, adding slice selection that will limit signal acquisition to any desired plane.

Sequence parameters can be selected to maximize the ratio of the iZQC signal ($S_{iZQC}$) to its root-mean-squareerror (RMSE), which has contributions from both thermal noise ($\sigma$) and confounding conventional single quantum coherences ($S_{SQC}$); i.e. $S_{iZQC}/\sqrt{\sigma^2+S_{SQC}^2}$ can be maximized.

With respect to the pulse sequence:
1. The pulse flip angles are 90°, 90°, 45°, 180°, 180°, . . . .
2. The first pulse creates an intermolecular double quantum coherence (iDQC); the second pulse transforms this to an intermolecular zero quantum coherence (iZQC); the third pulse transforms this to a two-spin single quantum coherence (SQC), which evolves into single-spin SQC which are measured by a series of echoes.
3. The first gradient (in conjunction with the third gradient) filters for iDQC and dictates the "correlation distance" $d_c=\pi/(\gamma G\delta)$, where G and $\delta$ are the first multi-quantum gradient amplitude and duration, respectively, and $\gamma$ is the gyromagnetic ratio. $d_c$ dictates the rough separation distance of the protons whose dipole-dipole interaction generates the quantum coherence. A typical value is $d_c$=50 µm, by setting $\delta$=2 ms and G=11.6 G/cm.
4. The frequency of the iZQC (and the resonance to neuronal currents) is then dictated by $d_c$ and the second gradient amplitude $G_{iZQC}$, independent of duration. This frequency=$\gamma G_{iZQC} d_c/(2\pi)$, which also can be put in terms of the ratio of the gradients: $G_{iZQC}/(2G\delta)$. A typical value would be in the 10s of Hz, e.g. 20 Hz when $G_{iZQC}$=0.93 G/cm and $d_c$=50 µm.
5. The shape of the pulses, starting with the third pulse, allow for imaging slice selection if desired.
6. Imaging gradients can be added as needed if desired.

Embodiments of the Invention that are General and Will be True if the Pulse Sequence Details/Parameters Change:

When using the current pulse sequence (diagrammed above in FIG. 2A), the resonant frequency (which dictates the sensitivity to corresponding neuro-electro-magnetic oscillations) is equal to $G_{iZQC}/(2G\delta)$. However, many elements of this sequence may change from optimization and experimental work. The essential element is that the frequency (and/or duration) of the iZQC, and thereby its sensitivity to neuro-electro-magnetic oscillations of the same frequency, will be controlled by the amplitude and/or duration of one or more applied magnetic field gradients of the types, for example, shown in FIG. 2B. This control of the iZQC frequency and duration is new. Previous iZQC methods had a resonant frequency dictated by one or more gradients, but it was not varied or tuned (or even recognized).

Although embodiments are described above with reference to applying the pulse sequence to a brain, the pulse sequence described in any of the above embodiments may alternatively be applied to a spine or nerves. Such alternatives are considered to be within the spirit and scope of the present invention, and may therefore utilize the advantages of the configurations and embodiments described above.

The method steps in any of the embodiments described herein are not restricted to being performed in any particular order. Also, structures or systems mentioned in any of the method embodiments may utilize structures or systems mentioned in any of the device/system embodiments. Such structures or systems may be described in detail with respect to the device/system embodiments only but are applicable to any of the method embodiments.

Features in any of the embodiments described in this disclosure may be employed in combination with features in other embodiments described herein, such combinations are considered to be within the spirit and scope of the present invention.

The contemplated modifications and variations specifically mentioned in this disclosure are considered to be within the spirit and scope of the present invention.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A method for magnetic resonance imaging, the method comprising:
applying a pulse sequence in vivo for exciting intermolecular zero-quantum coherence that is sensitive to neuro-electro-magnetic oscillations (NEMOs), wherein the pulse sequence comprises:
a plurality of radiofrequency (RF) pulses; and
a plurality of magnetic field gradients;
receiving, in response to applying the pulse sequence, signals associated with the intermolecular zero-quantum coherence excited by the pulse sequence; and
forming a magnetic resonance image of the NEMOs using the received signals,
wherein the intermolecular zero-quantum coherence excited by the pulse sequence comprises a frequency that is controlled by at least one of an amplitude or a duration of the plurality of magnetic field gradients based on a frequency of targeted NEMOs.

2. The method of claim 1, wherein the plurality of RF pulses comprises:
a first RF pulse for generating intermolecular double-quantum coherence in the NEMOs;
a second RF pulse for transforming the intermolecular double-quantum coherence into the intermolecular zero-quantum coherence; and
a third RF pulse for transforming the intermolecular zero-quantum coherence into intermolecular single-quantum coherence.

3. The method of claim 1, wherein the intermolecular zero-quantum coherence comprises a duration controlled by at least one of the amplitude or the duration of the plurality of magnetic field gradients.

4. The method of claim 1, wherein the frequency of the intermolecular zero-quantum coherence is the same as the frequency of the targeted NEMOs.

5. The method of claim 4, wherein the frequency of the intermolecular zero-quantum coherence is in a range of 100 Hz or less.

6. The method of claim 1, wherein the sensitivity to the NEMOs is essentially attributed to the intermolecular zero-quantum coherence.

7. The method of claim 1, wherein the intermolecular zero-quantum coherence is resonant at a difference of Larmor frequencies of two interacting spins of the intermolecular zero-quantum coherence.

8. The method of claim 1, wherein the applying, receiving, and forming steps are not sensitive to blood flow effects within a brain, water bound to macromolecules, or cell swelling.

9. The method of claim 1, wherein the applying, receiving, and forming steps are sensitive to only NEMOs.

10. A system for magnetic resonance imaging, the system comprising:
    coils that are configured to apply a pulse sequence in vivo for exciting intermolecular zero-quantum coherence that is sensitive to neuro-electro-magnetic oscillations (NEMOs), wherein the pulse sequence comprises:
        a plurality of radiofrequency (RF) pulses; and
        a plurality of magnetic field gradients;
    a receiver configured to receive signals associated with the intermolecular zero-quantum coherence excited by the pulse sequence; and
    a magnetic resonance imaging device configured to form a magnetic resonance image of the NEMOs using the received signals,
    wherein the intermolecular zero-quantum coherence excited by the pulse sequence comprises a frequency that is controlled by at least one of an amplitude or a duration of the plurality of magnetic field gradients based on a frequency of targeted NEMOs.

11. The system of claim 10, wherein the plurality of RF pulses comprises:
    a first RF pulse for generating intermolecular double-quantum coherence in the NEMOs;
    a second RF pulse for transforming the intermolecular double-quantum coherence into the intermolecular zero-quantum coherence; and
    a third RF pulse for transforming the intermolecular zero-quantum coherence into intermolecular single-quantum coherence.

12. The system of claim 10, wherein the intermolecular zero-quantum coherence comprises a duration controlled by at least one of the amplitude or the duration of the plurality of magnetic field gradients.

13. The system of claim 10, wherein the frequency of the intermolecular zero-quantum coherence is the same as the frequency of the targeted NEMOs.

14. The system of claim 13, wherein the frequency of the intermolecular zero-quantum coherence is in a range of 100 Hz or less.

15. The system of claim 10, wherein the sensitivity to the NEMOs is essentially attributed to the intermolecular zero-quantum coherence.

16. The system of claim 10, wherein the intermolecular zero-quantum coherence is resonant at a difference of Larmor frequencies of two interacting spins of the intermolecular zero-quantum coherence.

17. The system of claim 10, wherein the magnetic resonance image of the NEMOs is not sensitive to blood flow effects within a brain, water bound to macromolecules, or cell swelling.

18. The system of claim 10, wherein the magnetic resonance image of the NEMOs is sensitive to only NEMOs.

* * * * *